United States Patent [19]

Jarrett et al.

[11] Patent Number: 4,687,808

[45] Date of Patent: Aug. 18, 1987

[54] ACTIVATION OF BIOCOMPATIBLE POLYMERS WITH BIOLOGICALS WHOSE BINDING COMPLEMENTS ARE PATHOLOGICAL EFFECTORS

[75] Inventors: Robert D. Jarrett; G. Howard McCain, both of Painesville, Ohio

[73] Assignee: BioSpecific Technologies, Inc., Painesville, Ohio

[21] Appl. No.: 515,949

[22] Filed: Jul. 20, 1983

Related U.S. Application Data

[63] Continuation-in-part of Ser. No. 407,613, Aug. 12, 1982, abandoned, and Ser. No. 407,614, Aug. 12, 1982, abandoned.

[51] Int. Cl.$^4$ ............................................. C07D 251/02
[52] U.S. Cl. ..................................... 525/54.1; 604/4; 604/5; 604/6; 424/78; 427/2
[58] Field of Search ..................... 604/4, 5, 6; 424/16, 424/32, 33, 35; 427/2; 525/54.1

[56] References Cited

U.S. PATENT DOCUMENTS

| | | | |
|---|---|---|---|
| 3,826,678 | 7/1974 | Hoffman et al. | 604/5 |
| 4,059,685 | 11/1977 | Johnson | 525/54.1 |
| 4,061,141 | 12/1977 | Hyden et al. | 128/214 R |
| 4,182,750 | 1/1980 | Sullivan et al. | 604/5 |
| 4,192,748 | 3/1980 | Hyden | 210/87 |
| 4,222,907 | 9/1981 | Katz | 260/6 |
| 4,239,743 | 12/1980 | Sedlacek et al. | 424/1 |
| 4,272,549 | 6/1981 | Cavazza | 424/316 |
| 4,292,296 | 9/1981 | Parsons, Jr. | 424/1 |
| 4,305,926 | 12/1981 | Everse et al. | 424/14 |
| 4,357,311 | 11/1982 | Schutt | 525/54.1 |
| 4,362,155 | 12/1982 | Skurkovich | 604/6 |
| 4,430,229 | 2/1984 | Yamawaki et al. | 210/692 |

FOREIGN PATENT DOCUMENTS

| | | | |
|---|---|---|---|
| 1104110 | 6/1981 | Canada | 252/31 |
| 0082345 | 6/1983 | European Pat. Off. | |

OTHER PUBLICATIONS

McCullough et al, "Therapeutic Plasma Exchange", Lab. Med 12(12) p. 745 (1981).
Terman et al, "Extracorporeal Immunoadsorption: Initial Experience in Human Systemic Lupus Erythematosus", The Lancet, Oct. 20, 1979, pp. 824–826.
Terman et al, "Specific Removal of Circulated Antigen by Means of Immunoadsorption", FEBS Letters, vol. 61, No. 1, Jan. 1976, pp. 59–62.
Bansal et al, "Ex vivo Removal of Serum TgG in a Patient with Colon Carcinoma", Cancer, 42(1), pp. 1–18 (1978).
Malchesky et al, "On-Line Separation of Macromolecules by Membrane Filtraton with Cryogelation", Artif. Organs, 4:205(1980).
Terman et al, "Specific Removal of Bovine Serum Albumin (BSA) Antibodies in vivo by Extracorporeal Circulation Over BSA Immobilized on Nylon Microcapsules," J. of Immunology, vol. 116, No. 5, pp. 1337–1341 (1976).
Terman et al, "Specific Extraction of Antigen in vivo by Extracorporeal Circulation Over Antobody Immophilized in Colloidion-Charcoal," J. of Immunology, vol. 117, No. 5, pp. 1971–1975 (1976).
Terman et al, "Removal of Circulating Antigen and Immune Complexes with Immunoreactive Colloidion Membranes", FEBS Letters, vol. 68, No. 1(1976).
Ratner et al, "Synthetic Hydrogels for Biomedical Applications", ASC Symp. Ser. 1976, vol. 31, pp. 1–36.
A. S. Hoffman, "Use of Radiation Technology in Preparing Materials for Bioengineering and Medical Science", Ind. Appl. Radiosat. Radiat. Technol., Proc. Int. Conf., 1982, pp. 279–321.
Hoffman et al, "New Approaches to Non-Thrombogenic Materials", Coagulation: Curr. Res. Clin. Appl., Proc. Symp., 1972, pp. 201–226.

*Primary Examiner*—Morton Poelak
*Assistant Examiner*—Nathan M. Nutter
*Attorney, Agent, or Firm*—Thoburn T. Dunlap; William A. Skinner

[57] ABSTRACT

Biocompatible polymers containing immobilized biologicals which retain a high specificity for binding pathological effectors or specific groups of pathological effectors are disclosed.

14 Claims, No Drawings

ACTIVATION OF BIOCOMPATIBLE POLYMERS WITH BIOLOGICALS WHOSE BINDING COMPLEMENTS ARE PATHOLOGICAL EFFECTORS

CROSS-REFERENCE TO RELATED APPLICATION

This application is a continuation-in-part of copending applications Ser. Nos. 407,613 and 407,614, filed on Aug. 12, 1982 both now abandoned.

TECHNICAL FIELD

This invention relates to biocompatible polymers having immobilized reactive biologicals thereon which bind selected specific pathological effectors or specific groups of pathological effectors associated with diseased body fluids.

BACKGROUND OF THE INVENTION

The course of many disease states is often reflected by elevated levels of specific blood proteins and other molecules. This phenomenon is typically utilized as a diagnostic tool to define the pathology and to follow the course of clinical treatment. In many instances, these specific blood components are directly or indirectly responsible for the primary and secondary manifestations of the disease process. "Autoimmune" diseases can be described as diseases characterized by circulating antibodies to endogenous substrates and tissue proteins required by the body for normal growth and maintenance. "Neoplastic" diseases are typically characterized by uncontrolled growth of an undifferentiated transformed cell line which evades or comprises the body's natural defense mechanisms by producing immunosuppressant blocking factors, surface antigen masking components and/or growth regulator constituents. Specific compartmentalization of these pathological effectors (i.e., causitive agent) onto a biocompatible substrate is consistent with the restoration of "normal" body function by removal of the pathological effectors of the disease process.

The basic function of the organs, cells and molecules that comprise the immune system is to recognize and to eliminate from the body foreign substances. These foreign substances are eliminated by reaction between the foreign substance and antibodies which are formed in response to the substance. In general, this function is performed efficiently and without detriment to the host. However, in certain instances, disturbances can occur which can lead to pathogenic disorders such as, for example, an uncontrolled response (allergic disorders) or an abnormal response (autoimmune disease). The pathogenesis of both of these disorders is related directly or indirectly to the production of antibodies with cross reactivities to either environmental antigens (allergens) or self-antigens.

An autoimmune disease is a pathological condition arising when a host responds immunologically by production of antibodies with reactivity to a self-antigen. Autoimmunity can affect almost every part of the body, and generally involves a reaction between a self-antigen and an immunoglobulin (IgM or IgG) antibody. Representative autoimmune diseases can involve the thyroid, kidney, pancreas, neurons, gastric mucosa, adrenals, skin, red cells and synovial membranes as well as thyroglobulin, insulin, deoxyribonucleic acids and immunoglobulins.

For some types of autoimmune and neoplastic diseases, non-specific immunosuppressant treatments, such as whole body X-irradiation or the administration of cytotoxic drugs, have been used with limited success. The disadvantages of such treatment include the toxicity of the agents used, and the increased incidence of various cancers, especially lymphomas and reticulum cell sarcomas, following such therapy. In addition, the use of nonspecific agents for chronic cellular suppression greatly increases the susceptibility of the patient to serious infection from environmental fungi, bacteria and viruses which under ordinary circumstances would not cause problems. The invention disclosed herein is specific in that it removes only the pathological effector or those groups of pathological effectors which are related to and responsible for the manifestations of a particular disease.

In viewing the prior art, one finds that most recently there have been generally two approaches to therapeutic treatments for autoimmune and/or neoplastic diseases. The first of these is to introduce a material into the patient which causes a specific type of immunological tolerance to be produced. This suppression of antibody response would then effect a tolerance to the offending antigen. A typical example of this type of approach is U.S. Pat. No.4,222,907 issued to Katz on Sept. 16, 1981. In this reference, the diseased patient is given a therapeutic treatment which consists of introducing conjugates of an antigen linked to a D-glutamic acid: D-lysine copolymer.

The second approach has been the extracorporeal route. The procedures generally involve the removal of whole blood, separation of cellular and soluble blood substances, substitution or treatment of blood plasma and recombination-infusion of the treated whole blood. The first example of this approach would be plasma substitution or exchange with salt, sugar and/or protein solutions and is described by McCullough et al, "Therapeutic Plasma Exchange," Lab. Med. 12(12), p. 745 (1981). Plasma exchange is a rather crude technique that requires a large volume of replacement solution. A second example of this approach involves physical and/or biochemical modification of the plasma portion of whole blood. Typical of the state of the art of this therapeutic treatment are, for example, the Terman et al article "Extracorporeal Immunoadsorption: Initial Experience in Human Systemic Lupus Erythematosus," The Lancet, Oct. 20, 1979, pages 824–826. This article describes a hemodialysis type system utilizing two mechanical filters with a DNA collodian charcoal filter between said two mechanical filters. Typical of this state of the art, however, the adsorbant column is only semispecific for immune components because the charcoal substrate will nonspecifically delete many vital low molecular weight constituents from the treated plasma. A second application of this approach can be illustrated by the Terman et al article "Specific Removal of Circulated Antigen by Means of Immunoadsorption," FEBS Letters, Vol. 61, No. 1, January, 1976, pages 59–62. This reference teaches the specific removal of radiolabeled antigen by antibody treated cellulosic membranes. The author, however, demonstrates that control membranes have a significant capacity to non-specifically adsorb proteins.

A third application of this approach is illustrated by the Bansal et al article "Ex vivo Removal of Serum IgG in a Patient With Colon Carcinoma," Cancer, 42(1), pp. 1–18 (1978). This report teaches the semi-specific adsorption of immunoglobulin by ex vivo treatment of plasma with formalin and heat-killed *Staphylococcus aureas*. The biological activity of certain strains of *S. aureas* is attributed to a molecule present on the cell wall, called Protein A, which interacts and binds with the Fc portion of mammalian IgG. This treatment, because it interacts with the Fc moiety, does not discriminate between normal and pathological IgG components and experiments have shown the possibility of significant side effects.

A fourth application of this approach can be illustrated by the Malchesky et al article "On-line Separation of Macromolecules by Membrane Filtration With Cryogelation," Artif. Organs 4:205, 1980. This publication teaches the semi-specific removal of cryoglobulin substances from plasma by the combination of filtration and cold treatment chambers. The incidence and composition of cryoglobular precipitates are not necessarily consistent with or indicative of many autoimmune or neoplastic diseases.

Another problem associated with the current state of the art is that without systems using mechanical filtration, the specific pathological effectors desired to be removed have not been removed in large enough amounts to do much good for the diseased patient in that the columns do not specifically absorb substantially only the desired specific pathological effectors.

It has now been found that high specificity of pathological effector removal can be effectuated by treatment of blood and/or plasma in an economical manner using the present invention.

SUMMARY OF THE INVENTION

Broadly stated, this invention relates to a biospecific polymer having immobilized reactive biologicals, said biologicals having high specific activity for binding complements which are pathological effectors comprising a biocompatible polymer support, with or without a spacer attached to said biocompatible polymer support having a physical size which forces said spacer to extend from the surface of said biocompatible polymer support, and a biological or biologicals immobilized on the biocompatible polymer support or the spacer, via chemical bonding, and characterized in that said biological or biologicals retain their reactivity for binding specific pathological effectors or specific groups of pathological effectors.

This invention also relates to a regimen for the therapeutic treatment of autoimmune diseases comprising passing a diseased patient's blood, plasma or other body fluid over a biospecific polymer having immobilized reactive biologicals, thereby removing the desired pathological effectors from said patient's blood or plasma and then returning said blood to said patient.

Further, this invention, broadly stated, relates to a method of producing these biospecific polymers having immobilized reactive biologicals which have high specific activity for binding complements which are pathological effectors.

Also relating to this invention is a method of producing biospecific polymers on a mechanical support to provide excellent mechanical integrity.

These and other objects of the present invention are disclosed and described in the detailed description below and in the appended claims.

DETAILED DESCRIPTION

I. BIOCOMPATIBLE POLYMER SUPPORT

The biocompatible polymer supports useful in the present invention are materials which tend not to cause adverse effects when in contact with body fluids such as, for example, plasma or whole blood, while at the same time maintaining a reactive but immobilized biological oriented such that the biological is extended out from the surface of said polymer support. The materials which are suitable are those which may be cast into films and other physical forms, while at the same time being susceptible to having said biologicals chemically bound to them without damaging either themselves or the biologicals bound thereto. The types of materials generally contemplated to be suitable are those known in the art as hydrogels and may be either copolymers or homopolymers.

Modified cellulose and cellulosic derivatives, particularly cellulose acetate, have also found utility as biocompatible supports useful in the present invention. By modified cellulosic derivatives what is meant is that the cellulosic polymer is surface modified by covalently linking pendant biocompatible surface groups to the cellulosic substrate polymer rendering it more biocompatible. Such surface groups are well known and need not be described here, however, for purposes of the present invention, albumin has shown particular utility as a modifying group. Methods of attaching such groups are described hereinbelow.

Homopolymers may also be used as suitable biocompatible polymer supports in the present invention. It is to be understood, however, that when homopolymers are discussed, they include materials which can also be identified as slightly cross-linked homopolymers. That is, they contain a relatively small amount of a second component either intrinsic in the production of the monomer or added purposely to insure enough crosslinking so as to protect the homopolymer from slowly dissolving away in an aqueous media, such as blood. An example of this type of homopolymer which is often slightly crosslinked is hydroxyethyl methacrylate (HEMA).

Referring to the hydrogels, suitable polymers may either be regular homopolymers containing substantially no other material in their matrices, or they may be copolymers prepared from two or more monomers such as styrene and vinyl acetate, for example. In certain instances, this type of tailoring of the copolymers with various monomers may enhance the desirable properties of the biocompatible polymer support material. Examples of suitable monomers which may be copolymerized, include, for example, hydroxyethyl methacrylate and glycidyl methacrylate.

Also useful are terpolymers which are a subclass of copolymers containing three monomers which are polymerized. An example of a suitable terpolymer is glycidyl methacrylate/N-vinyl pyrrolidone/hydroxyethyl methacrylate (GMA/NVP/HEMA).

In addition to the specific copolymers and homopolymers listed above, copolymers, prepared with or without various additional monomers, and homopolymers suitable in the present invention may be polymerized from the following monomers: hydroxyalkyl acrylates and hydroxyalkyl methacrylates, for example, hydroxyethyl acrylate, hydroxypropyl acrylate, and hydroxybutyl methacrylate; epoxy acrylates and epoxy methacrylates, such as, for example, glycidyl methacrylate; amino alkyl acrylates and amino alkyl methacrylates; N-vinyl compounds, such as, for example, N-vinyl pyrrolidone, N-vinyl carbazole, N-vinyl acetamide, and N-vinyl succinimide; amino styrenes; polyvinyl alcohols and polyvinyl amines, which must be made from suitable polymeric precursors; polyacrylamide and various substituted polyacrylamides; vinyl pyridine; vinyl sulfonate and polyvinyl sulfate; vinylene carbonate; vinyl acetic acid, and vinyl crotonic acid; allyl amine and allyl alcohol; vinyl glycidyl ether and allyl glycidyl ether. Processes and procedures for creating copolymers and/or homopolymers from the above monomers are well-known and understood in that particular art. These parameters are not critical to the instant invention with the caveat that the final copolymer and/or'-homopolymer is nontoxic for animal, including human, use.

The method used to cast these materials into a form suitable for use in the present invention is not of critical importance. One presently preferred method is spin casting and is exemplified in Examples 2, 3 and 4.

II. BIOLOGICALS

In the context of the present invention, biological and/or biologicals may be defined as a chemical compound which possesses an ability to covalently bond to the biocompatible polymer support or spacer (defined hereinbelow), while at the same time retaining an activity to bind a desired pathological-causing constituent. It is to be understood that, in addition, the biological or biologicals employed must be of such size that they covalently bond to the surface of the polymer support and are not small enough to penetrate the porous matrix of the polymer support and be chemically bonded therefore inside or in the interior of the support material. In this light, a spacer may be employed to insure that the reactive site of the biological, which remains and is susceptible to bonding with the desired pathological constituent, can in fact be presented to this constituent, i.e., that it is held outward away from the support so as to come into contact with the body fluid flowing over the support. It is obvious from the above that, of course, the reactivity for binding the desired pathological constituent is, in fact, retained after immobilization of the biological or biologicals onto the biocompatible polymer support. Examples of materials which may be used as biologicals include, for example: acetylcholine receptor proteins, histocompatibility antigens, ribonucleic acids, basement membrane proteins, immunoglobulin classes and subclasses, myeloma protein receptors, complement components, myelin proteins, and various hormones, vitamins and their receptor components. Particular examples are, for example, attaching insulin to a biocompatible polymer support to remove anti-insulin antibody which is associated with the autoimmune disease insulin resistance; attaching anti-Clq and/or Clq to a biocompatible polymer support to remove immune complexes which are associated with connective tissue and proliferative diseases such as, for example, rheumatoid arthritis and carcinoma.

Any generally known method of chemical attachment will suffice for attaching the biologicals to the biocompatible polymer support, with the caveat that the biological still has at least one active site for the particular autoimmune disease-associated component. Generally, the methods of chemical attachment used fall into three classes or routes of attachment. These three routes are, (1) spontaneous attachment, (2) chemical activation of terminal functional groups, and (3) coupling reagent attachment. Spontaneous covalent attachment of biologicals to polymer support surface proceeds via chemically reactive groups extending from the polymer support. Thus, for example, reactive groups such as aldehyde and epoxy extending from the polymer support readily couple biologicals containing available hydroxyl, amino or thiol groups. Also, for example, free aldehyde groups on the polymer support couple via acetal linkages with hydroxyl-containing biologicals and via imide linkages with amino-containing molecules. Additionally, for example, free oxime groups couple via alkylamine, ether and thioether linkages with biologicals containing amine, hydroxyl and thio groups respectively. For purposes of convenience all said attachments and couplings are defined herein as immobilizations. More extensive discussions of these reactions may be found, for example, in "Chemical for Enzyme Immobilization of Porous Cellulose Beads" Chen, L. F. et al, Biotechnology and Bioengineering, Vol. XIX , pp. 1463–1473 (1977) and "Epoxy Activated Sepharose," 6B, Pharmacia Fine Chemicals, Affinity Chromatography, pp. 27–32 (1979).

Chemical activation of terminal functional groups may be accomplished by activating polymer surface functional groups by chemical modification of their terminal components. This method can be exemplified by the oxidation of terminal epoxy functions with periodic acid to form active aldehyde groups. This method is further exemplified, for example, in "Immobilization of Amyloglucosidose on Poly [(Glycidyl Methacrylate) Co (Ethylene Dimethacrylate)]Carrier and Its Derivatives," Svec, F. et al, Biotechnology and Bioengineering, Vol. XX, pp. 1319–1328 (1978). The immobilization of the biologicals proceeds as described hereinabove. Condensation reactions may be accomplished between free carboxyl and amine groups via carbodiimide activation of the carboxy groups as is described, for example, in "New Approaches to Non-Thrombogenic Materials," Hoffman et al, *Coagulation-Current Research and Clinical Applications,* Academic Press, N.Y. (1973). Briefly the immobilization of the biologicals is effected by carbodiimide activation by either the polymer or biological carboxyl groups and condensation with a free amine to form a stable peptide bond. The final orientation of the biological is generally a factor as to whether an amine or a carboxyl containing polymer be utilized.

Coupling reagent attachment can be accomplished using a variety of coupling agents to form covalent bridges between polymers and biologicals. Here free hydroxyl and/or amine containing polymers and biologicals are covalently coupled by reagents such as, for example, cyanogen bromide, diisocyanates, dialdehydes and trichloro-s-triazine. More exhaustive discussion of this technique may be found for example, in the Chen et al article cited hereinabove.

The preferred method of immobilizing a reactive biological onto a biocompatible polymer substrate in a given case generally is dictated by the molecular locations of the reactive binding moiety of the biological and the functional groups on the biological and polymer substrate which can be covalently combined. For example, it is presently preferred in the case of polymer substrates containing terminal hydroxy functions to activate by treatment with an alkaline solution of cyanogen bromide (10 to 20% wlr). Typically mixture is maintained at room temperature (20° to 25° C.) The reaction for about 30 minutes. The pH of the solution is maintained in a range of about 10 to 12, by the addition of alkaline material, e.g., KOH or NaOH. The polymer is extensively washed with physiological saline (0.9 gm%) and incubated with solutions of a purified biological dissolved in a slightly alkaline buffer solution for 12 to 16 hours at 2° to 8° C. The polymer is extensively rinsed with physiological saline to remove unbound or nonspecifically bound biological components.

Biologicals are immobilized on glycidyl containing polymers via ether, thioether or alkylamine bonds. Epoxy-activated polymer substrates are rinsed and swollen with aqueous neutral buffer solutions at room temperature. Purified biologicals, dissolved borate, carbonate or phosphate buffer solutions are incubated with the glycidyl polymer substrate for 12 to 20 hours at 4° to 30° C. Excess and nonspecifically bound biologicals are removed by rinsing the polymer with saline, acetic acid (0.2 to 1.0 M) and phosphate-buffered (pH=7.2±0.2) saline solutions. Activation of amine and carboxyl containing polymer matrices are effected by treatment with purified biologicals dissolved in slightly acidic (pH 4.5 to 6.5) buffer solutions of a water soluble carbodiimide. Biologicals are covalently coupled to polymer support substrates by incubation of polymer support, biological and carbodiimide reactants for 12 to 16 hours at 2° to 8° C. The polymer-biological conjugates are washed alternately in acid then alkaline rinses until the rinse solutions are clear of biological and carbodiimide reactants.

In order to determine the specific binding characteristics of the polymer immobilized biologicals, physiological serum solutions of complementary biomolecules were treated with activated membranes. The amounts of biomolecule were measured radiochemically. Significant reduction of specific biomolecules resulted following brief exposures to the biologically modified polymer substrates.

III. SPACERS

In the present invention, a spacer may be defined as a molecule or compound which is capable of attachment to the surface of a biospecific polymer support, is large enough to extend from the surface of said support and is capable of immobilizing a biological and/or biologicals. The spacer insures that the active site of the biological is held outward away from the support so as to contact the body fluid more efficiently. It is obvious from the above that, of course, the reactivity for binding with the desired disease complex is, in fact, retained after immobilization of the biological or biologicals onto the spacer and therefore onto the biocompatible polymer support.

The spacers are derived from organic molecules having at least two reactive functional groups generally situated at opposing ends of the molecule. Such groups serve as attachment vehicles capable of coupling the spacer to the polymer support and to the biological. The reactive functional groups on the spacer may be the same or different with the caveat that they react with functional groups along the surface of the polymer support and the functional groups extending from the biological forming covalent bonds. Any known method for carrying out such coupling reactions will suffice. For example, the methods described hereinabove outlining coupling routes for attaching a biological directly onto a polymer support may be used.

Suitable examples of spacers which may be used in the present invention, where the reactive functional groups are the same, include, for example, 1,6-diaminohexane, glutaraldehyde, 1,4-cyclohexane-dicarboxylic acid, ethylenediamine tetraacetic acid, triethylene glycol, 1,4-butanediol diglycidyl'ether, methylene-p-phenyl diisocyanate and succinic anhydride. Examples of spacers in which the reactive functional groups are not the same include, for example, 6-aminocaproic acid, p-nitrobenzoyl chloride, 1,2-epoxy-3-(p-nitrophenoxy) propane, aminopropyltriethoxy-silane and homocysteine thiolactone.

Polypeptides and proteins may also be used as spacers in the present invention. Albumin, a low affinity protein, for example, has been successfully employed as a spacer. In addition, albumin and other natural proteins serve to render the polymer support more biocompatible.

Finally, it is understood that certain materials may act simultaneously as a spacer and as the activator in the reaction used to combine the spacer and the biocompatible support. Examples of these kinds of compounds, include, for example, gluteraldehyde and 1,4-butanediol diglycidyl ether.

IV. SUPPORT MEMBER

Most, if not all, of the suitable biocompatible polymer supports have very low mechanical stability. Most of these materials are, in fact, gels or gel-like as opposed to materials which have high mechanical stability, such as, for example, sheets of polypropylene. Thus, in most embodiments utilizing the present invention, a support member which is mechanically stable is necessary. This support member allows large surface areas to be utilized to insure rapid and medically, as well as commercially, acceptable levels of immune disease-associated component removal. The support member, besides being mechanically stable, should also be inexpensive and must be sterilizable so as to be made compatible for use in a system wherein the blood of a diseased patient is to be treated by the present invention. Examples of materials which are suitable for the present inventron as support members include, for example, filter paper, polyester fiber, polycarbonates, reticulated polyurethanes, NORYL®, a polyphenylene oxide polymer manufactured by the General Electric Company, microporous polyolefins such as polypropylene, and cotton cloth.

Many methods of attaching the activated membrane or biocompatible polymer support having biologicals chemically attached may be utilized. Thus, for example, methods such as spin coating, horizontal casting, vacuum impregnating, dip coating, dip coating with later crosslinking, and solution copolymerization may be used. Specific examples of these methods may be found in the examples hereinbelow.

V. THERAPEUTIC REGIMEN

Broadly stated, the presently contemplated therapeutic regimen of the present invention is for the therapeutic treatment of autoimmune and other diseases comprising exposing a diseased patient's blood or plasma having a biospecific polymer having immobilized reactive biologicals, thereby removing the specific pathological effectors from said patient's blood or plasma and then returning said blood to patient. This therapeutic treatment may or may not necessitate the use of blood separation techniques. Thus the treatment is contemplated to be carried out in a manner similar to a dialysis treatment with the advantage that total blood separation may not be needed and that there is very little if any physical damaging of normal blood components.

It is also possible, of course, to utilize the present invention and the process of the present invention in the treatment of plasma. The plasma may be obtained from whole blood by any of the currently known and practiced methods. Thus, for example plasma may be separated from a patient's blood by known methods, then treated by the present invention and then recombined with the other blood components and returned to the patient using currently known procedures. In addition plasma which is being used in known medical treatments may utilize the present invention to treat said plasma before being administered to a patient requiring plasma from a blood bank for example. Obviously whole blood from a blood bank may also be treated by and benefit from the present invention.

It is also to be understood that the current invention may also be used with other body fluids to effect removal of pathological effectors.

Because of the advantages of the present invention mentioned above as well as others which will be clear to a person skilled in this art many types of disease states are contemplated to respond to the present invention used in a therapeutic regimen. Broadly stated six groups of disease states could be advantageously treated. These six disease categories are disorders of immune components, drug excesses, toxin exposure, imbalances of body substances, infections, and neoplastic states. Many diseases are currently treated using plasmapheresis and cytopheresis where the desired result is removal of a specific substance. The present invention and the process of the invention would apply to these diseases currently treated by plasmapheresis and cytopheresis.

Examples of immune complex diseases which can be treated are, for example, any disease states involving antibody, antigen, antibody-antigen, antigen-antigen and antibody-antibody interactions, cell surface complexes, cytoplasmic complexes, etc.

Examples of drug overdoses which can be treated are, for example, overdoses of iron, dioxin, aspirin, TYLENOL, methotrexate and other tricyclics Examples of poisons and toxins for which the present invention is suitable are, for example, lead, aluminum, mushrooms (Anatoxin) and organic phosphates.

Body substances when present in excess can lead to disease. Examples of these which can be eliminated using the present invention include, for example, cholesterol, uric acid, immunoglobulins, sickle cells, uremic toxins, bilirubin, porphyrin, cortisol and prostaglandins.

Some examples of infectious agents which may be treated are, for example, viral disorders such as cytomegalovirus; protozan disorders such as malaria, trypanosomes and leishmanias; bacterial infections such as strepotococci; fungus infections such as tinea versicolor; mycoplasma such as pleuro-pneumonia-like organisms; rickettsia diseases such as typhus and spotted fevers; spirochetes such as syphilis and chlamydia-agents in the psittacosis lympho-granuloa-trachoma disease group.

Neoplasms which are treatable using the present invention include, for example, the lymphomas, sarcomas, carcinomas and leukemias. These may be removed by specific removal of a cell line, inhibitors, initiators of the disease and combinations thereof.

Further examples of disease states which may be treated using the present invention include, for example, the following:

Infections such as; Post streptococcal glomerulonephritis, Subacute bacterial endocarditis, Secondary syphilis, Pneumococcal sepsis, Lepromatous leprosy, Ventricular shunt infection, Infectious mononucleosis, Typhoid fever, Subacute sclerosing encephalitis, Landry-Guillain-Barre syndrome, Hepatitis B infection, Quartan malaria, Schistosomiasis, and Trypanosomiasis.

Neoplasmas such as; Hepatoma, Lymphoma and Hodgkins disease, Acute leukemia, Hypernephroma, Carcinoma of the colon, Bronchogenic carcinoma., and Burkitts lymphoma.

Connective Tissue Disorders such as; Periarteritis nodosa, Chronic glomerulonephritis, Acute or subacute thyroiditis, Vinyl chloride poisoning, Chronic liver disease, Mixed cryoglobulinemias, Berger's disease or IgA nephropathy, Rapidly progressive glomerulonephritis, and Sickle cell anemia.

Hematologic Diseases such as; Thrombic thrombocytopenic purpura, Autoimmune hemolytic anemia, Idiopathic thrombocytopenic purpura, Idiopathic neutropenia, Cold hemagglutinin disease, Paroxysmal cold hemoglobinuria, Circulating anticoagulants, Acquired hemophilia, the leukemias, the lymphomas, Erythroblastosis fetalis, Pernicious anemia, and Rh diseases.

Neurologic Diseases such as; Acute demyelinating encephalitis, Multiple Sclerosis, Landry's paralysis, Guillain-Barre syndrome, Peripheral neuritis, and Myasthenia gravis.

Collagen Diseases such as; Raynaud's, Lupus Erythematosus, Polyarteritis nodosa, Scleroderma, Dermatomyositis, Sjogren's syndrome, Rheumatoid arthritis, Rheumatic fever, and Erythema nodosa.

Endocrine Diseases such as, for example; Cushing's syndrome & disease, Thyroiditis, Thyrotoxicosis, Addison's disease, and Aspermatogenesis.

Gastrointestinal Diseases such as; Portal cirrhosis, Acute hepatitis, Chronic active hepatitis, Lupoid hepatitis, Biliary cirrhosis, Ulcerative colitis, Regional enteritis, and Pancreatitis.

Miscellaneous Diseases such as, for example; Hypercholesterolemia, Glomerulonephritis, Basement membrane disease, Psychogenic states—drugs, Postaortic valve prosthesis—hemolytic anemia, Exfoliative dermatitis, Id reaction, Psoriasis, Behcet's syndrome, Carcinoma, Subacute bacterial endocarditis, Hypertension, Asthma, Hereditary angioneurotic edema, Meningococcemia, Crohn disease, Hepatic encephalopathy and Raynaud disease.

Further, Diseases characterized by Antibodies to Nuclear Antigens, Cytoplasmic Antigens, Cell Surface Antigens, and Subclasses may be treated by the present invention. Suitable examples include, for example; Antibodies to Native—DNA (double stranded) or single and double stranded, Antibodies to SS DNA, Antibodies to Deoxyribonucleoprotein, Antibodies to Histone, Antibodies to Sm, Antibodies to RNP, Antibodies to Sc 1-1 Scleroderma, Antibodies to SS—A Sjogren syndrome, Sicca complex, Antibodies to RAP—Rheumatoid Arthritis, Sjogren syndrome, Antibodies to PM—1 Polymyositis-dermatomyositis, and Antibodies to nucleolar-Systemic sclerosis, Sjogren syndrome.

Also, Antibodies Associated With Specific Autoimmune Disorders such as; Antibodies to smooth muscle—Chronic Hepatitis, Antibodies to acetylcholine receptors—Myasthenia gravis, Antibodies to basement membrane at the dermal—epidermal junction—Bullous pemphigoid, Antibodies to the mucopolysaccharide protein complex or intracellular cement substance Pemphigus, Antibodies to immunoglobulins Rheumatoid arthritis, Antibodies to glomerular basement membrane Glomerulonephritis, Goodpasture's syndrome, Idiopathic primary hemasiderosis, Antibodies to erythrocytes—Autoimmune hemolytic anemia, Antibodies to the thyroid Hashimoto's, Antibodies to intrinsic factor Pernicious anemia, Antibodies to platelets—Idiopathic thrombocytopenic purpura, Alloimmunization, Antibodies to mitochondria—Primary biliary cirrhosis, Antibodies to salivary duct cells—Sjogren's syndrome, Antibodies to the adrenal—Idiopathic adrenal atropathy, Antibodies to thyroid microsomal—Grave's Disease, Antibodies to thyroglobulin —Addison's Disease, and Antibodies to islet cells—Diabetes Mellitus.

Paraproteinemias such as, for example; Multiple myeloma, Macroglobulinemia, Cryoglobulinemia, and Light chain disease, Hyperlipidemia such as; Primary biliary cirrhosis and Familial Hypercholesterolemia.

Endocrinopathies such as; Grave disease and Diabetes mellitus.

Alloimmunization such as; Hemolytic disease of the newborn and Renal homograft rejection.

Also, suitable for treatment using the present invention include, for example, Post Transfusion Purpura and Autoantibody Diseases such as, Goodpasture's syndrome, Myasthenia gravis, Pemphigus vulgaris, Hematological disease, Idiopathic (autoimmune) thrombocytopenic purpura, Autoimmune hemolytic anemia, Inhibitor to factor VIII and Polyradiculopathy/Guillain-Barre Syndrome.

Immune Complex Diseases may also be treated and include, for example; Systemic Lupus Erythematosus, Polyarteritis nodosa, Cutaneous vasculitis, Rheumatoid arthritis, Glomerulonephritis, and Dermatomyositis.

While not subscribing to any one particular theory over another a review of the probable progression of autoimmune pathology suggests that the pathological sequence is very likely initiated by a free antigen challenge, followed by antibody evolution and complexing and finalized by antibody excess and complement fixation of formed complexes. Thus, for proper selection of the biospecific polymer formulation and provision for proper efficacy would require preliminary diagnostic procedures to determine the predominant form of the autoimmune effector. An illustrative example of this is described below for the treatment of rheumatoid disease. Briefly, rheumatoid disease can be characterized as following the progression from (a) free RF antigen (atypical Ig) (rheumatic condition), (b) free RF antibody evolution and RF complexing and finally (c) antibody excess and complement activated RF complex fixation. Thus treatment of rheumatoid disease in its early development could be determined by detection of atypical immunoglobulins by monoclonal rheumatoid factor (mRF) antibodies. Treatment at this stage would be best effected by m-RF activated biospecific polymers to remove the offending antigen and thus preventing the evolution of endogenous RF (e-RF) antibodies. Diagnostic evidence of e-RF would indicate the utilization of biospecific polymers having both m-RF and aggregated gamma globulin active biologicals (RF antigen). Alternatively, two biospecific polymers in series, each having one type of active biological could be utilized. In either case this combination of m-RF and aggregated gamma globulin would adsorb both the offending antigen and antibody molecules to sequester the disease progression. In the case where significant levels of RF antigen—antibody complex is detected, biospecific polymers containing Clq and/or collagen effector molecules would be indicated. Finally, if the disease process has progressed to the stage of complement fixation of formed immune complexes an effective biospecific polymer would contain one or more anti-complement antibodies such as, for example, anti-Clq, anti-$C_3$ or anti-$C_4$. Again the biologicals, if more than one is desirable, can be immobilized on a single biocompatible support or each can be on a separate support and connected in series in relation to the blood or plasma flow.

As has been proposed above, effective use of the present invention is realized by thorough definition of the dynamics and stage of the immune response for effective disease management.

Today, plasmapheresis and cytophoresis are the treatments for disease by removal of noxious substances or cells from the blood. It is currently believed that any disease treated by plasmapheresis and/or cytopheresis, where the desired result is the removal of a specific substance, can be advantageously treated with the product and process of the present invention.

More specifically, a presently contemplated therapeutic regimen for whole blood may be illustrated as follows:

(a) a vascular access is provided which will allow for;

(b) a blood flow of from about 30 ml/min. to about 200 ml/min., (c) an anticoagulant is administered to the blood; and (d) a pumping means is provided;

(e) the blood is passed in contact with the present invention;

(f) depending of the anticoagulant used, additional medication may be needed or desired to neutralize the anticoagulatory effect on said treated blood;

(g) the treated blood is returned to the patient.

The time frame presently contemplated for the above regimen is approximately from about 2 hours to about 4 hours. It is realized, of course, that depending upon the situation such time frame may be either shortened or lengthened.

A presently contemplated therapeutic regimen for plasma may be illustrated as follows:

(a) a vascular access is provided which will allow for;

(b) a blood flow of from about 30 ml/min. to about 200 ml/min., (c) an anticoagulant is administered to the blood; and (d) a pumping means is provided;

(e) a plasma-formed blood component separation means is provided;

(f) the plasma is passed in contact with the present invention;

(g) filtration through a 0.2 micron filter to remove any microemboli, bacteria and/or fungi;

(h) the treated plasma and the formed blood components are recombined;

(i) depending on the anticoagulant used, additional medication may be needed or desired to neutralize the anticoagulating effect on said treated blood;

(j) the treated blood is returned to the patient.

The vascular access may be provided using well known techniques and procedures in the medical arts. Thus, for example, an indwelling large bore cannula may be used intravenously or arterially. Examples of suitable veins and arteries include the antecubital vein, subclavian vein and brachial or radial arteries. It is further understood that an arterial venous shunt or fistulae (AV shunt) may also be used. In this case the heart is the pumping means. If an AV shunt or fistulae is not used the preferred pumping means during venous access is a roller-peristalic pump capable of providing a flow rate of from about 30 ml/min to about 200 ml/min.

Suitable anticoagulants useful in the process of the present invention include, for example, acid citrate dextrose (approximately 1 ml to every 8 ml of whole blood), heparin, heparin/acid citrate dextrose mixtures (e.g. 1250 IU heparin in 125 ml acid citrate dextrose/L), and prostaglandin. It is to be appreciated that in using anticoagulants such as heparin and prostaglandin it is generally understood that a counteracting medication should be administered to the treated blood or plasma before returning or giving said blood or plasma to a patient.

Further, in the case of treating plasma, it is understood that any conventional methods of removing the formed blood components may be used. Suitable examples of methods of separating plasma from formed blood components include, plasmapheresis, centrifugal cell separation, and cell sedimentation in a plasma bag. Where possible both continuous separation and intermittent (batch) separation are suitable—the aforementioned methods of separation are independent of the present invention and its use.

Finally, the form of the present invention is, generally, not critical. Thus the present invention may utilize a biocompatible support containing the biological in the form of sheets, hollow fibers, cylindrical fibers, reticular networks, cylindrical or rectangular channels, beads and combinations thereof for example. The use of a fluidized bed may also be advantageous in some cases.

EXAMPLE 1

This example describes one method of casting the biocompatible polymer support and a method of chemically attaching a biological directly to the polymer support. This example also is used to describe the use of a system having no mechanical support associated with it.

ABSORPTION OF ANTI-INSULIN ANTIBODIES USING INSULIN ACTIVATED POLY-HYDROXYETHYL METHACRYLATE (p-HEMA) MEMBRANE

A. Polymer casting.

Solutions of monomer were prepared by combining 15.0 g 2-hydroxyethyl methacrylate (Polysciences Inc., Warrington, PA), 15.0 g ethylene glycol (Fisher Scientific, Pittsburg, PA), 0.08 g sodium bisulfite (Fisher) and 0.036 g ammonium persulfate (Fisher). The solution was stirred for 15 minutes at room temperature. Approximately 5 ml of solution was placed on a glass plate (5"1×5"w×⅜"t) in the center of a polyethylene spacer (10 mil thick) cut to form a gasket with a 4"×4" window. A second glass plate was placed over the gasket and solution, clamped in place and the entire assembly incubated at 60° C. overnight. The clamps were removed and the glass plates were pried slightly apart and transferred to a deionized water bath for at least 24 hours. The swollen polymer membrane was carefully removed from the glass plates and was rinsedhydrated for at least three days in fresh exchanges of deionized water (500 ml per day).

B. Polymer activation

Membrane discs (5 mm diameter were cut from the polymer sheet for activation and analysis. A 10–20 gm % cyanogen bromide (Eastman Kodak Co., Rochester, NY) solution was prepared by dissolving 1.69 g of finely divided BrCN crystals in 10 ml of 0.2 M $Na_2CO_3$ (pH 11.1) with continuous stirring at 4° C. The pH of the solution was maintained above 11 by the dropwise addition of 5N NaOH until the crystals were dissolved and the pH was stabilized. Four membrane discs were placed in a small sieve and rinsed with approximately 5 ml 0.1 N HCl and incubated for 15 minutes in the cyanogen bromide solution. The discs were each rinsed at least two more times with 5 ml portions of 0.1 N HCl and incubated overnight in 5.0 ml U-100 regular ILETIN ® insulin injection solution (Eli Lilly, Indianapolis, Ind.) which had been adjusted to a pH of 8.7 by the addition of 1 N NaOH. The membrane discs were rinsed with 5 ml 0.5 M NaCl, 0.1M $Na_2CO_3$ solution and 3 times in 5 ml aliquots of phophate (0.05M) buffered saline (0.9 gm %) solution (pH=7.4).

C. Evaluation of membrane adsorption of anti-insulin antibody.

A double antibody competitive binding radioimmunoassay was performed by incubating 560 pg (picogram) $I^{125}$ labeled porcine insulin (New England Nuclear, Boston, MA) and serial dilutions (980 to 15 pg) of non labeled porcine insulin (Cambridge Nuclear, Billerica, MA) or the p-HEMA membrane discs with 280 pg of guinea pig anti-porcine insulin antibody (New England Nuclear) in 0.5 ml of phosphate (0.05 M) buffered (pH 7.4) saline (0.9 gm %) containing 1 gm % Bovine Serum Albumin (Sigma Chemical Co., St. Louis, MO) for two hours at room temperature. The p-HEMA discs were removed from each test solution. A 0.1 ml aliquot of goat anti-guinea pig gamma globulin was added to each test tube. The test solutions were mixed and incubated for an additional two hours at room temperature. A 1.0 ml aliquot of cold (2°-4° C.) phosphate buffered saline (pH 7.4) was added to each tube. Each test solution was mixed and centrifuged for 15 minutes at 4° C. at 7500G and the supernatant decanted into 20 ml scintillation vials. The supernatant was gelled with 5.0 ml Aquasol liquid scintillation fluid (New England Nuclear) and counted in an Isocap 300 Counter (Searle Analytic Inc., DesPlaines, IL) for 4.0 minutes. Insulin treated membrane discs adsorbed 111pg anti-insulin antibody from solution or 283 per sq. cm. surface area.

EXAMPLE 2

This example describes how an unsupported biospecific membrane may be produced. It also describes how 6-aminocaproic acid (having a six carbon chain) may be used as a spacer for attaching insulin to the biocompatible polymer support used to remove insulin antibody and adsorption of anti-insulin antibodies using the insulin activated poly-hydroxyethyl methacrylate (p-HEMA) membrane.

A. Polymer casting.

Solutions of monomer were prepared by combining 15.0 g 2-hydroxyethyl methacrylate (Polysciences Inc., Warrington, PA), 15.0 g ethylene glycol (Fisher Scientific, Pittsburg, PA), 0.08 g sodium bisulfite (Fisher) and 0.036 g ammonium persulfate (Fisher). The solution was stirred for 15 minutes at room temperature. Approximately 5 ml of solution was placed on a glass plate (5"1×5"w×⅜"t) in the center of a polyethylene spacer (10 mil thick) cut to form a gasket with a 4"×4" window. A second glass plate was placed over the gasket and solution, clamped in place and the entire assembly incubated at 60° C. overnight. The clamps were removed and the glass plates were pried slightly apart and transferred to a deionized water bath for at least 24 hours. The swollen polymer membrane was carefully removed from the glass plates and was rinsed-hydrated for at least three days in fresh exchanges of deionized water (500 ml per day).

B. Polymer activation.

Membrane discs were prepared as previously described in Example 1. A 10-20 gm % cyanogen bromide (Eastman Kodak Co., Rochester, NY) solution was prepared by dissolving 1.69 g of finely divided BrCN crystals in 10 ml of 0.2 M $Na_2CO_3$ (pH 11.1) with continuous stirring at 4° C. The pH of the solution was maintained above 11 by the dropwise addition of 5N NaOH until the crystals were dissolved and the pH was stabilized. Four membrane discs were placed in a small sieve and rinsed with approximately 5 ml 0.1 N HCl and incubated for 15 minutes in the cyanogen bromide solution. The discs were each rinsed at least two more times with 5 ml portions of 0.1 N HCl and incubated overnight in 10 ml of a 10 gm % 6-aminocaproic acid solution (w/v) (Sigma chemical Co.) prepared in 0.1 M $Na_2CO_3$, 0.5 M NaCl buffer solution, pH 8.6. Membrane discs were rinsed with 5 ml 0.1 M $Na_2CO_3$, 0.5 M NaCl buffer and three 5 ml aliquots of phosphate (0.05 M) buffered (pH=7.4) saline (0.9 gm %) solution. The membrane discs were removed from the rinse solution, activated by incubation in 10 ml of a 10% (w/v) 1-cyclohexal-3-(2 morpholinoethyl) carbodiimide (Sigma Chemical Co.) solution prepared in 0.1 M (2[N-morpholino]ethanesulfonic acid) (MES) buffer (pH 6.0) for thirty minutes at room temperature and each disc rinsed in 5 ml of cold (4° C.) phosphate buffered saline solution. Duplicate membrane discs were incubated overnight in 5.0 ml of either U-100 regular ILETIN insulin injection solution or pork insulin regular ILETIN solutions (Eli Lilly, Indianapolis, IN) at 4° C. Membrane discs were removed from the protein solutions and rinsed three times in 5 ml of phosphate buffered saline solution.

C. Evaluation of membrane adsorption of anti-insulin antibody.

A double antibody competitive binding radioimmunoassay was performed by incubating 560 pg $I^{125}$ labeled porcine insulin (New England Nuclear, Boston, MA) and serial dilutions (980 to 15 pg) of non labeled porcine insulin (Cambridge Nuclear, Billerica, MA) or p-HEMA membrane discs with 280 pg of guinea pig anti-porcine insulin antibody (New England Nuclear) in 0.5 ml phosphate (0.05 M) buffered (pH 7.4) saline (0.9 gm %) containing 1 gm % bovine serum albumin (Sigma Chemical Co., St. Louis, MO) for two hours at room temperature. The p-HEMA discs were removed from each test solution. A 0.1 ml aliquot of goat anti-guinea pig gamma globulin was added to each test tube. The test solutions were mixed and incubated for an additional two hours at room temperature. A 1.0 ml aliquot of cold (2-4° C.) phosphate tuffered saline (pH 7.4) was added to each tube. Each test solution was mixed and centrifuged for 15 minutes at 4° C. at 7500 G and the supernatant decanted into 20 ml scintillation vials. The supernatant was gelled with 5.0 ml Aquasol liquid scintillation fluid (New England Nuclear) and counted in an Isocap 300 Counter (Searle Analytic Inc., DesPlaines, IL) for 4.0 minutes. Insulin treated membrane discs adsorbed 271 pg anti-insulin antibody from solution or 690 pg per sq. cm. surface area.

EXAMPLE 3

This example describes a method of casting the biocompatible polymer supports, both with and without mechanical support, via spin casting. This example also describes a second way of chemically binding the biological to the biocompatible polymer support.

ADSORPTION OF ANTI-HUMAN IMMUNOGLOBULIN G(IgG) ANTIBODIES (RHEUMATOID TYPE "FACTORS") USING IMMUNOGLOBULIN ACTIVATED POLY-HYDROXYETHYL METHACRYLATE-CO-GLYCIDYL METHACRYLATE (p-HEGL) MEMBRANES

I. Polymer casting.

The following example describes the production of both supported and unsupported polymer membranes by spin casting techniques.

A. Spin Casting Device

The spin casting device consists of a closed aluminum drum with ¼ in. thick walls. The inside dimensions of the drum are 4 in. in diameter and 5 in. in length. The drum is connected to a motor (Fisher Dyna-Mix; Fisher Scientific Co., Pittsburg, PA) which spins the drum, and the drum rpm is measured with a strobe phototachometer (Model 1891M Power Instrument Inc., Skokie, IL). A heat-blower gun (Fisher Scientific Co.) heats the spinning drum; thermocouples measure the internal drum temperature and the temperature of the air flowing over the drum. The drum is purged with nitrogen before and during the polymerization.

B. Supported Membrane Production

Whatman Grade 50 hardened filter paper (Fisher Scientific, Pittsburg, PA) was used as a support backing to provide mechanical strength for these spin castings. The paper was cut into rectangular sheets (415/16 × 127/16 in.) and then soaked in ethylene glycol (EG) (Fisher Scientific Co., Cat. No. E-177) for 30 min. at room temperature. The excess glycol was drained from the paper; after draining, the paper contained 2-4 g of EG. The conditioned paper was curled in the form of a cylinder and placed inside of the spin casting drum. The outside edge of the paper was pressed against the drum wall to expel any air between the wall and the paper. When the paper is in place, it is preferable but not necessary that the ends of the paper are butted up against each other; there can be some overlap. The paper backing was checked for entrapped air pockets; if any existed, they were removed with a rubber policeman.

For polymerizations which produce a very adhesive polymer, the spin casting cylinder can first be lined with a sheet of silicon release paper by placing the nontreated side of the paper against the cylinder. The conditioned Whatman filter can then be placed against the release paper carefully so as not to entrap air.

C. Polymerization Formulations

The following are representative polymerization formulations currently being used. In each case, the initiator was stirred with the reactive monomer(s) at room temperature for 30 minutes or until the initiator dissolved.

| GMA-HEMA (50/50) Copolymer | |
|---|---|
| 6.25 g | 2-Hydroxyethyl Methanoxylate (HEMA) |
| 6.25 g | Glycidyl Methacrylate (GMA) |
| 12.5 g | Ethylene Glycol (EG) |
| 0.02 g | 2,2'-Azobis(2-amidinopropane) Hydrochloride (ABAP) |
| GMA-NVP-HEMA (50/40/10) Copolymer | |
| 6.25 g | GMA |

-continued

| | | |
|---|---|---|
| 1.25 g | NVP | |
| 5.00 g | HEMA | |
| 12.5 g | EG* | |
| 0.02 g | ABAP | |

*The ethylene glycol weight includes 2-4 g of EG on the Whatman paper.

D. Spin Casting Procedure

While the initiator was dissolving in the monomer(s), the drum was loaded into the spin casting assembly. The drum was spin at 1400 rpm at room temperature and purged with nitrogen for 15 minutes after which the initiator-monomer solution (25.0 ml) was injected into the drum with a hypodermic syringe having a flexible Teflon tip. The nitrogen purge was resumed and the drum speed increased to 2,900 rpm.

The fan (ca. 35 ft$^3$/min.) and heater on the heat gun were started, and the drum was heated at 70°–75° C. for 90 minutes. The heat was then shut off, but the fan was left on to cool the drum until the internal drum temperature dropped to about 30° C. The cool drum was removed from the spin casting apparatus and filled with deionized water. After soaking for an hour, the casting was removed from the drum.

II. Polymer activation.

Membrane discs were prepared as previously described in Example 1. Fourteen individual discs were each incubated in 1.0 ml of 1.0 M hexane diamine (Eastman Kodak, Rochester, N.Y.) solution for 72 hours at 4° C. The discs were removed from the hexane diamine solution and washed three times with 2 ml phosphate buffered saline solution. A 4.0 gm % human gamma globulin (HGG) (Sigma Chemical Co.) solution was prepared by dissolving 4.0 gm HGG in 100 ml 0.1 M MES buffer (pH 6.0) solution with gentle stirring at room temperature. After the protein was completely dissolved, serial dilutions were made by successive transfers of 1.0 ml protein solution to 9.0 ml MES solution to yield protein concentrations of 4 mg/ml, 400 ug/ml, 40 ug/ml and 4 ug/ml of buffer. Two individual polymer discs were each incubated in 0.5 ml of the protein solutions and 0.5 ml of a 0.25 M 1-ethyl-3-(3-dimethyl-aminopropyl) carbodiimide (Sigma Chemical Co.) solution prepared in MES buffer for 72 hours at 4° C. Each membrane disc was removed from the protein solution and rinsed 3 times with 2 ml of cold (4° C.) phosphate buffered saline.

III. Evaluation of membrane adsorption of anti-IgG antibody from physiological solutions.

A radioimmunoassay was performed by incubating individual membrane discs with 10 ng I$^{125}$ goat anti-human IgG (New England Nuclear) in 1.0 ml PBS which contained 1.0 gm % Human Serum Albumin (Sigma Chemical Co.) for two hours at room temperature. The radiotracer solution was removed and each membrane was rinsed three times with 2.0 ml PBS solution. The membranes were incubated in the last rinse solution overnight at 4° C. Individual membranes were removed from the rinse solutions and counted in an Innotron Hydragamma counter (Scientific Products) for one minute each. Counts per minute were converted to disintegrations per minute (DPM) by division with the detector efficiency. The amount of adsorbed antibody was approximated by dividing the average DPM by the radiotracer specific activity. The following results were obtained:

| HGG Treatment (mg/ml) | Anti IgG Adsorbed (pg per sq. cm.)* |
|---|---|
| 20.0 | 2453 |
| 2.0 | 1919 |
| 0.2 | 1271 |
| 0.02 | 664 |
| 0.002 | ** |

*Picograms of radiotracer material per square centimeter of membrane.
**Background activity.

EXAMPLE 4

This example shows the use of amino caproic acid as a spacer for gamma-globulin.

Adsorption of anti-human Immunoglobulin G (Ig G) antibodies (Rheumatoid type "Factors") using immunoglobulin activated poly-hydroxyethyl methacrylate-co-glycidyl methacrylate (p-HEGL) membranes.

A. Polymer casting.

Spin Cast p-HEGL membranes were prepared as described in Example 3

B. Polymer derivatization and activation.

Membrane discs were prepared and treated as described in Example 3 except that 1.0 M 6-amino caproic acid (Sigma Chemical Co.) was substituted for hexane diamine as a derivitization and spacer agent.

C. Evaluation of membrane adsorption of anti-IgG antibody from physiological solutions.

A radioimmunoassay was performed as described in Example 3 and the following results were obtained:

| HGG Treatment (mg/ml) | Anti IgG Adsorbed (pg per sq. cm.)* |
|---|---|
| 20.0 | 2395 |
| 2.0 | 1828 |
| 0.2 | 1310 |
| 0.02 | 732 |
| 0.002 | 158 |

*Picograms of radiotracer material per square centimeter of membrane.

EXAMPLE 5

This example shows the use of albumin (67,000 MW) as a spacer for folate. The folate is used to remove folic acid binding protein.

Adsorption of Folic Acid Binding Proteins (FABP) by Folate-Albumin activated poly hydroxyethyl methacrylate (p-HEMA) membranes:

A. Polvmer Casting.

Filter paper supported p-HEMA polymer membranes were spin cast as described in Example 2 utilizing the following polymer formulation:

15.0 g: 2-Hydroxyethyl Methacrylate
15.0 g: Ethylene Glycol
0.08 g: Sodium Metabisulfite
0.036 g: Ammonium Persulfate B. Polymer derivatization and activation.

A folic acid Bovine Serum Albumin complex was prepared by carbodiimide condensation of folate carboxyl groups with albumin terminal amine groups. To achieve this 200 mg folic acid (Sigma Chemical Co.) was dissolved in 8 ml 0.1 N NaOH and 400 mg 1-cyclohexyl-3(2-morpholinoethyl)carbodiimide metho-p-toluenesulfonate (Sigma Chemical Co.) was dissolved in 2.0 ml 0.1 M MES buffer (pH 6.0) and 1.0 gm Bovine Serum Albumin (BSA) was dissolved in 40.0 ml 0.1 M MES buffer. The solutions were combined, mixed and incubated for 72 hours at 4° C. The unreacted folate and carbodiimide was removed from solution by treating 20 ml of the mixture with 20 ml of a BSA (2.5 gm %)—charcoal (1.25 gm %) suspension for thirty minutes at 4° C. The suspension was centrifuged for 15 min. at 3400 G at 4° C. decanted and filtered through a 0.22 micron filter.

Membrane discs were prepared and treated with cyanogen bromide solution as previously described in Example 1. After the discs were rinsed in cold saline solution, sets of eight discs were added to and incubated in 20 ml of either physiological saline, 160 mg % BSA or the folate albumin complex solution previously prepared. The discs were incubated for 72 hours at 4° C. Each membrane set was removed from solution, blotted dry and placed in 20 ml saline solution at 4° C. to rinse for at least 24 hours. Duplicate membranes were treated with 8 ml of 1% gluteraldehyde solution for 1 minute and rinsed overnight in 20 ml of phosphate buffered saline buffer.

C. Evaluation of membrane adsorption of folic acid binding protein (FABP) from physiological solution.

A competitive protein binding radioassay was performed by incubating 370 pg $^3$H-pteroylglutamic Acid (PGA) (Amersham Corp., Arlington Heights, IL) and standard dilutions (48 to 348 pg) of non-radioactive PGA (Sigma Chemical Co.) or p-HEMA membrane discs with 234 pg binding activity of FABP (Kamen, B. A. and Caston, J. D., "Direct Radiochemical Assay for Serum Folate: Competition between $^3$H-Folic Acid and 5-Methyl-tetrahydrofolic Acid for a Folate Binder", J. Lab. Clin. Med., 83, 164, 1974) in 1.0 ml of 0.05 M phosphate buffer (pH 7.6) which contained 20 ul of folate free normal human serum and 5 mg sodium ascorbate (Sigma Chemical Co.). The radioassay tubes were mixed, incubated for 30 minutes at room temperature and 10 minutes at 4° C. Individual membrane discs were removed from the test solutions and 0.5 ml of a cold (4° C.) BSA (2.5 gm %)—charcoal (1.25 gm %) suspension was added to each tube. All test solutions were incubated for 10 minutes at 4° C. and centrifuged at 2000 G for 15 minutes at 4° C. The supernatants were decanted into 20 ml scintillation vials. Twelve (12.0) ml liquid scintillation fluid (Fisher Scientific, Pittsburg, PA) was added to each vial. Samples were counted in an Isocap 300 Counter (Searle Analytic Inc.) for 2 minutes each. The following results were obtained:

| Membrane Treatment | FABP Adsorbed (pg/sq. cm.) |
| --- | --- |
| Saline | 67 |
| Cyanogen Bromide | 54 |
| Bovine Serum Albumin | 39 |
| Folate BSA Complex | 758 |

The above-described examples serve to illustrate the present invention without restricting it in any way. It will be obvious to those in the art that various changes and modifications may be made without departing from the spirit and scope of the present invention.

What is claimed is:

1. A biospecific polymer comprising:
   (a) a biocompatible terpolymer support comprising glycidyl methacrylate, N-vinylpyrrolidone and hydroxyethyl methacrylate; and
   (b) a biological or biologicals immobilized on said terpolymer support via chemical bonding and wherein said biological or biologicals retain their reactivity for adsorbing specific pathological effectors or specific groups of pathological effectors.

2. A biospecific polymer comprising:
   (a) a biocompatible terpolymer support comprising glycidyl methacrylate, N-vinylpyrrolidone and hydroxyethyl methacrylate;
   (b) a spacer bonded to said biocompatible terpolymer support; and
   (c) a biological or biologicals immobilized on said spacer via chemical bonding and wherein said biological or biologicals retain their reactivity for adsorbing specific pathological effectors or specific groups of pathological effectors.

3. A biospecific polymer as claimed in claims 1 or 2 further characterized in that said terpolymer support is fixed to a mechanically stable support member.

4. A biospecific polymer as claimed in claim 3 wherein said mechanically stable support member is selected from the group consisting of polyester fiber, microporous polyolefins, cotton cloth, polystyrene, polycarbonate, polyphenylene oxide, reticulated polyurethanes and combinations thereof.

5. A biospecific polymer as claimed in claims 1 or 2 wherein said biologicals are selected from the group consisting of acetylcholine receptor proteins, histocompatibility antigens, ribonucleic acids, basement membrane proteins, immunoglobulin classes and subclasses, myeloma protein receptors, complement components, myelin proteins, hormones and their receptor components and, vitamins and their receptor components.

6. A biospecific polymer as claimed in claims 1 or 2 wherein said biological is insulin used to remove anti-insulin antibody which is associated with the autoimmune disease insulin resistance.

7. A biospecific polymer as claimed in claims 1 or 2 wherein said biological is purified gamma globulin used to remove immune components which are associated with connective tissue and proliferative diseases such as rheumatoid arthritis and carcinoma.

8. A biospecific polymer as claimed in claim 2 wherein said spacer is selected from the group consisting of 1,6-diaminohexane, glutaraldehyde, 1,4-cyclohexanedicarboxylic acid, ethylenediamine tetraacetic acid, triethylene glycol, 1,4-butanediol diglycidyl ether, methylene-p-phenyl diisocyanate, 6-aminocaproic acid, p-nitrobenzoyl chloride, 1,2-epoxy-3-(p-nitrophenoxy) propane, aminopropyltriethoxy-silane, succinic anhydride, homoapteine thiolactone and albumin.

9. A therapeutic treatment of diseases which comprises passing a diseased patient's body fluid contact with a biospecific polymer comprising a biocompatible terpolymer support comprising glycidyl methacrylate, N-vinylpyrrolidone and hydroxyethyl methacrylate having immobilized reactive biologicals where said biologicals adsorb specific pathological effectors or groups of pathological effectors associated with said patient's disease state and returning said body fluid to said patient.

10. A therapeutic treatment of diseases which comprises passing a diseased patient's body fluid in contact with a biospecific polymer comprising a biocompatible terpolymer support comprising glycidyl methacrylate, N-vinylpyrrolidone and hydroxyethyl methacrylate, a spacer attached to said biocompatible terpolymer support and a biological immobilized on said spacer wherein said biologicals adsorb specific pathological effectors or specific groups of pathological effectors associated with said patient's disease state and returning said body fluid to said patient.

11. A therapeutic treatment of diseases which comprises passing a body fluid which is to be administered to a patient, prior to said body fluid being administered to said patient, in contact with a biospecific polymer comprising a biocompatible terpolymer support comprising glycidyl methacrylate, N-vinylpyrrolidone and hydroxyethyl methacrylate having immobilized reactive biologicals, thereby adsorbing and removing specific pathological effectors from said body fluid, and then introducing said body fluid to said patient.

12. A therapeutic treatment of diseases which comprises passing a body fluid which is to be administered to a patient, prior to said body fluid being administered to said patient, in contact with a biospecific polymer comprising a biocompatible terpolymer support comprising glycidyl methacrylate, N-vinylpyrrolidone and hydroxyethyl methacrylate, a spacer attached to said biocompatible terpolymer support and a biological immobilized on said spacer, thereby removing specific pathological effectors from said body fluid, and then introducing said body fluid to said patient.

13. A therapeutic treatment as claimed in claims 9, 10 or 11 wherein two or more biospecific polymers each having the same or different reactive biologicals or groups of biologicals immobilized thereon are utilized in series to remove said specific pathological effectors.

14. The therapeutic method as recited in claim 9, 10, 11 or 12 wherein the body fluid to be treated is selected from the group consisting of blood, whole blood, blood plasma, and cerebrospinal fluid.

* * * * *